United States Patent
Pronk et al.

(10) Patent No.: US 7,052,458 B2
(45) Date of Patent: May 30, 2006

(54) MEDICAL DIAGNOSTIC SYSTEM

(75) Inventors: Bernardus Johannes Pronk, Eindhoven (NL); Ivo Jacobus Mathieu Canjels, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 10/121,781

(22) Filed: Apr. 12, 2002

(65) Prior Publication Data

US 2002/0165698 A1   Nov. 7, 2002

(30) Foreign Application Priority Data

Apr. 13, 2001 (EP) .................................. 01201354

(51) Int. Cl.
*A61B 5/00* (2006.01)
(52) U.S. Cl. ................... 600/300; 600/407; 709/218
(58) Field of Classification Search ............... 600/407, 600/410, 300, 425; 378/207; 382/117, 128, 382/141; 705/2; 128/897, 920; 709/217–219, 709/221

See application file for complete search history.

(56) References Cited

U.S. PATENT DOCUMENTS

| | | | |
|---|---|---|---|
| 4,991,193 A * | 2/1991 | Cecil et al. | 378/117 |
| 5,054,044 A | 10/1991 | Audon et al. | |
| 5,870,450 A * | 2/1999 | Khutoryansky et al. | 378/197 |
| 6,094,589 A * | 7/2000 | Schmitt | 600/407 |
| 6,353,445 B1* | 3/2002 | Babula et al. | 345/733 |
| 6,377,162 B1* | 4/2002 | Delestienne et al. | 340/286.07 |
| 2003/0216625 A1* | 11/2003 | Phipps | 600/300 |
| 2004/0039605 A1* | 2/2004 | Bardy | 705/2 |
| 2004/0077934 A1* | 4/2004 | Massad | 600/300 |

FOREIGN PATENT DOCUMENTS

| | | |
|---|---|---|
| DE | 42 25 834 A1 | 2/1994 |
| EP | 0 370 791 A1 | 5/1990 |
| EP | 0 450 462 A2 | 10/1991 |

* cited by examiner

*Primary Examiner*—Ruth S. Smith
(74) *Attorney, Agent, or Firm*—Thomas M. Lundin

(57) ABSTRACT

A medical diagnostic system, for example, an X-ray examination apparatus, comprises a local group of functions which are only locally adjustable and a global group of functions which can be remotely adjusted. Preferably, functions in both groups can be remotely installed, but the functions in the local group can be activated only locally. Preferably, local activation is performed on the basis of an authorization.

5 Claims, 1 Drawing Sheet

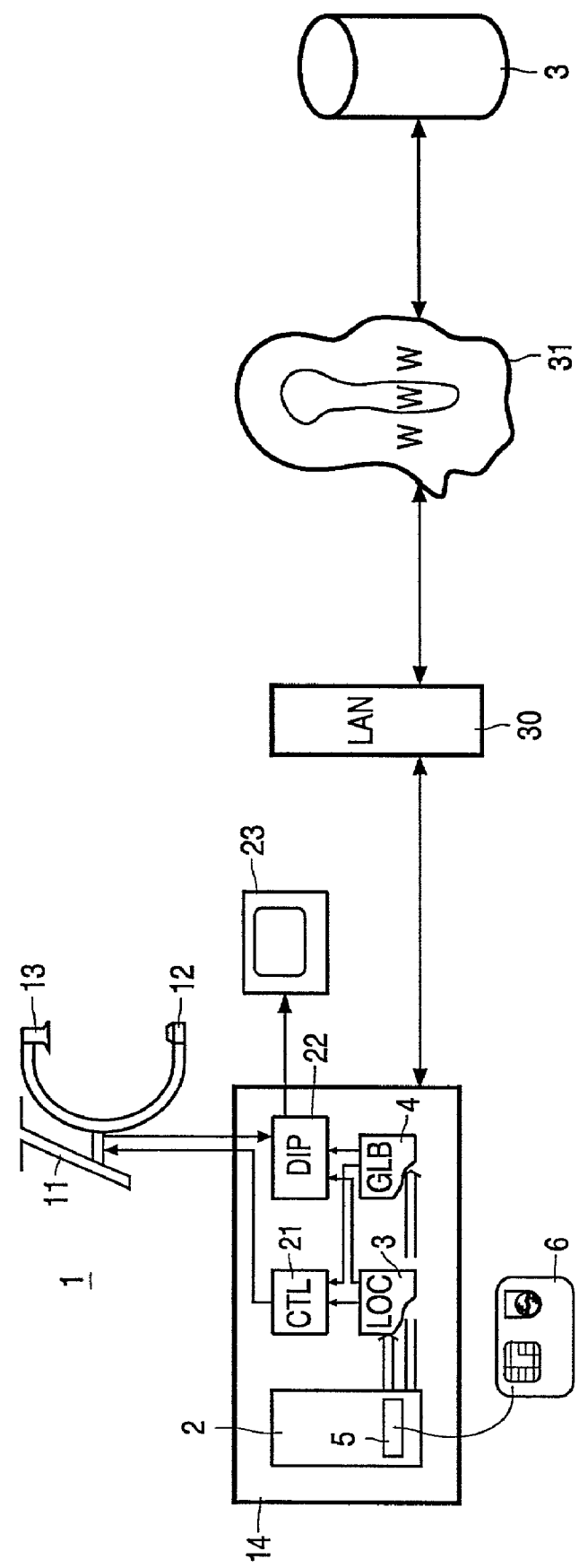

MEDICAL DIAGNOSTIC SYSTEM

The invention relates to a medical diagnostic system which comprises a plurality of adjustable functions.

A medical diagnostic system is, for example, a diagnostic workstation in which an image processing program is installed. The medical diagnostic system is connected to a local network. New versions of the image processing program are stored in a server computer of the maker of the image processing program. The local network communicates with the server computer via the Internet. The server computer checks whether the image processing program installed in the known diagnostic workstation is the most recent version. If a newer version is available in the server computer, the server computer downloads the more recent version into the known diagnostic workstation via the Internet and the local network whereto the known medical diagnostic system is connected; the server computer subsequently provides "re-booting" of the relevant diagnostic workstation so as to activate the more recent version of the image processing program. The image processing function is thus remotely adjusted. In practice only a small adaptation of the image processing function installed in an earlier version can be carried out in the diagnostic workstation.

It is an object of the invention to provide a medical diagnostic workstation in which functions other than image processing can additionally be remotely adjusted and in which the activation of new adjustments is managed better.

This object is achieved by means of a medical diagnostic system in accordance with the invention in which:
 a local group of adjustable functions can be adjusted only at the site of the medical diagnostic system, and
 a global group of adjustable functions can be adjusted on the basis of communication with a service center remote from the medical diagnostic system.

In accordance with the invention adjustable functions in the local group can be adjusted only at the site of the medical diagnostic system. It is thus achieved that the adjustable functions in the local group can be adjusted only in authorized form. On the other hand, in accordance with the invention it is possible to perform adjustments of adjustable functions which do not involve a risk remotely by taking up such no-risk adjustable functions in the global group.

The adjustable functions in the global group can be remotely adjusted. It is thus achieved that adjustable functions whose installation is not problematic or risky need not be installed at the site of the medical diagnostic system.

The medial diagnostic system is, for example, an X-ray examination apparatus which includes an X-ray source. Adjustable functions whose adjustment necessitates activation of the X-ray source are taken up in the local group in accordance with the invention. Risks related to the remote activation of the X-ray source are thus avoided. Adjustable functions for which a stand of the X-ray apparatus is put into motion are also taken up in the local group. The risks relating to the unsupervised putting into motion of the stand are thus avoided.

These and other aspects of the invention will be described in detail hereinafter with reference to the following embodiments which are defined in the dependent claims.

The medical diagnostic system in accordance with the invention is preferably provided with an installation platform. Such an installation platform is a software platform which enables installation of a variety of adjustable functions on the basis of software. For example, the installation platform is arranged for remote installation of adjustable functions of the local group in the medical diagnostic system such that the new adjustment is not yet activated. Such activation can take place on site at a later stage, that is, under supervision, the new adjustment then already being completely ready as if it were in the medical diagnostic system.

The medical diagnostic system in accordance with the invention is preferably arranged to carry out the adjustments on the basis of an authorization. Separate authorizations are feasible for the global group and for the local group. When use is made of such authorizations, the new adjustments of the medical diagnostic system can be managed better. For example, the authorization may be made dependent on the level of training of the person performing the adjustment. An authorization can also be issued on the basis of the rights held by the user of the medical diagnostic system, for example, in dependence on whether the new adjustment has already been paid for.

For verification of the authorization the installation platform is preferably provided with a read unit capable of receiving a data carrier. The authorization stored on the data carrier is read from the data carrier by the read unit. The installation platform enables the adjustment of adjustable functions in the local group on the basis of the authorization read. Moreover, it may be that the installation platform activates previously installed adjustments on the basis of the authorization read. In conformity with this aspect of the invention the data carrier is held by the user, for example, a service technician. The authorization on the data carrier is dependent on the level of training and/or experience of the bearer.

DRAWINGS

These and other aspects of the invention will be described in detail hereinafter, by way of example, with reference to the following embodiments and the accompanying drawing; therein:

FIG. 1 is a diagrammatic representation of a medical diagnostic system in accordance with the invention.

DESCRIPTION

FIG. 1 shows diagrammatically a medical diagnostic system in accordance with the invention. The medical diagnostic system concerns an X-ray examination apparatus 1 in the present example. The X-ray examination apparatus 1 includes a stand 11 wherefrom an X-ray source 12 and an X-ray detector 13, for example, an X-ray image intensifier television camera or a digital X-ray detector, are suspended. The X-ray examination apparatus also includes a data processor 14. The data processor 14 includes a control unit 21 and a data processing unit 22. The installation platform 2 is also included in the data processor 14. The control unit 21 controls the activation of the X-ray source 12 and the positioning and motion of the stand 11. The control unit 21 is loaded with control programs whereby the X-ray examination apparatus is controlled automatically to a high degree. The X-ray detector forms an image signal, for example, an electronic video signal (EVS) from the X-ray image. The data processing unit 22 carries out image processing steps on the image signal. To this end, image processing programs are loaded into the data processing unit so as to process the image signal. The processed image signal is applied to a monitor 23 for display of the processed image. It is alternatively possible to store the processed image signal in a memory of the data processing unit.

The control unit 21 and the data processing unit 22 utilize programs with instructions for carrying out the various adjustable functions of the X-ray examination apparatus 1. The data processor 14 of the X-ray examination apparatus is connected to a local network 30, for example, the internal IT network of the hospital in which the X-ray examination apparatus is installed. The service center 3 and the local network 30 are both coupled to the world-wide web. The X-ray examination apparatus 1 can be supervised from the service center, for example, for remote evaluation of the image quality while the X-ray apparatus is in operation. Furthermore, the functions in the global group can be activated from the service center. It is also possible to install new functions in the global group 4 as well as in the local group 3 from the service center. The installation platform communicates, via the world-wide web, with a server computer of the service center 3. The server computer delivers software for a new function or revised software for already installed functions. The newly installed functions in the local group can be activated only on site and with a valid authorization. To this end, for example, the user or a service technician inserts his chip card 6 on which the authorization is stored into the read unit 5 of the installation platform 2. The installation platform enables the newly installed functions for activation on the basis of the authorization read. For example, the generator of the X-ray source is enabled so as to activate the X-ray source for the emission of X-rays, for example, in order to form an X-ray image of a test phantom. It is also possible to put the stand 11 into motion and to activate new control software for the stand drive.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A medical diagnostic system comprising:
    a data processor which is controlled by functions including a local group of adjustable functions and a global group of adjustable functions;
    means for installing an adjustment to the local group of adjustable functions, and
    means for installing an adjustment to the global group of adjustable functions;
    local activating means for activating the installation of the adjustment to the local group of adjustable functions, said activating being performed only at the site of the medical diagnostic system; and
    global activating means for activating the installation of the adjustments to the global group of adjustable functions, said global activating being from one of: a remote service center or from the site of the medical diagnostic system.

2. A medical diagnostic system as claimed in claim 1, wherein the means for installing an adjustment to the local group of adjustable functions comprises an installation platform for adjusting the adjustable functions, the installation platform enabling the installation of remotely adjustable functions.

3. A medical diagnostic system as claimed in claim 2, further comprising an activation means by which the remotely installed functions are activated at the site of the medical diagnostic system on the basis of an authorization.

4. A medical diagnostic system as claimed in claim 3, in which the installation platform is provided with a read unit for receiving the authorization from a data carrier.

5. A medical diagnostic system as claimed in claim 1, further comprising authorization means by which the adjustments in the local group and/or the global group are activated on the basis of an authorization.

* * * * *